United States Patent
Robinson et al.

(10) Patent No.: US 6,416,744 B1
(45) Date of Patent: Jul. 9, 2002

(54) TOOTH WHITENING CHEWING GUM

(75) Inventors: Richard S. Robinson, Belle Mead; John P. Curtis, Phillipsburg; Donna M. Vroom, Kendall Park; Bernie L. Blackwell, Ringoes; Rolando M. Catiis, Rahway, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/886,901

(22) Filed: Jun. 21, 2001

(51) Int. Cl.$^7$ .............. A61K 9/68; A61K 9/16; A61K 33/30
(52) U.S. Cl. .......... 424/48; 424/49; 424/440; 424/641; 424/642; 424/643; 426/3; 426/5
(58) Field of Search .............. 424/49–58, 440, 424/48, 641–643; 426/3, 5

(56) References Cited

U.S. PATENT DOCUMENTS

| | | | | |
|---|---|---|---|---|
| RE33,465 E | * | 11/1990 | Eby | 514/494 |
| 5,037,637 A | * | 8/1991 | Gaffar et al. | 424/52 |
| 5,059,416 A | * | 10/1991 | Cherukuri et al. | 424/48 |
| 5,260,062 A | * | 11/1993 | Gaffar | 424/401 |
| 5,324,751 A | * | 6/1994 | DuRoss | 514/777 |
| 5,589,160 A | * | 12/1996 | Rice | 424/49 |
| 5,603,920 A | * | 2/1997 | Rice | 424/49 |
| 5,651,958 A | * | 7/1997 | Rice | 424/49 |
| 5,658,553 A | * | 8/1997 | Rice | 424/49 |
| 5,676,932 A | * | 10/1997 | Wason et al. | 424/49 |
| 5,716,601 A | * | 2/1998 | Rice | 424/52 |
| 5,855,871 A | * | 1/1999 | Masters et al. | 424/49 |
| 5,869,028 A | * | 2/1999 | McGill et al. | 424/49 |
| 6,030,605 A | * | 2/2000 | D'Ameila et al. | 424/48 |
| 6,290,933 B1 | * | 9/2001 | Durga et al. | 424/49 |

* cited by examiner

Primary Examiner—Shep K. Rose
(74) Attorney, Agent, or Firm—Paul Shapiro

(57) ABSTRACT

A tooth whitening chewing gum composition effective to remove stains from teeth is prepared from a mixture of a chewing gum base, plasticizing, sweetening, flavoring agents, and about 0.5 to about 5.0% by weight of a silica particles, the particles containing about 5 to about 35% by weight water and having a mean particle size from 5 to 12 microns; an Einlehner hardness of from 1 to 20; an oil absorption value of from 40 to less than 100 cc/i 00g; and, a BET surface area from 100 to 700 m$^2$/g of silica.

6 Claims, No Drawings

TOOTH WHITENING CHEWING GUM

BACKGROUND OF THE INVENTION

1. Field of the Invention

This invention relates generally to a chewing gum composition which when chewed by an individual acts to remove stains and whiten tooth enamel.

2. Prior Art

A tooth is comprised of an inner layer and an outer hard enamel layer that is the protective layer of the tooth. The enamel layer of a tooth is naturally an opaque white or d slightly off-white color. It is this enamel layer that can become stained or discolored. The enamel layer of a tooth is composed of hydroxyapatit mineral crystals that create a somewhat porous surface. It is believed that this porous nature of the enamel layer is what allows staining agents and discoloring substances to permeate the enamel and discolor the tooth. Many substances that an individual comes in (contact with on a daily basis can "stain" or reduce the "whiteness" of his or her teeth. In particular, foods, tobacco products and fluids such as tea and coffee tend to stain the teeth. These produces or substances accumulate on the enamel layer of the tooth and form a pellicle film over. the teeth. These staining and discoloring substances can then permeate the enamel layer.

Clean, white teeth are considered to be very desirable by most people in Western countries. Dull-looking, stained teeth are socially objectionable both on the basis of cosmetic appearance and also as an indication of poor oral hygiene.

There are available in the marketplace toothpaste compositions for home use which contain 1–3% b weight of peroxygen compounds such as hydrogen peroxide which when applied in a toothbrushing regimen effect whitening or removal of stains. However these toothpaste compositions are not convenient to use when outside the home.

A tooth stain-removing chewing gum which helps to keep teeth white has wide appeal to the general public. The product would be especially beneficial and convenient for use immediately after consuming stain-inducing foods, coffee, tea, red wine, and tobacco products. Since the chewing of gum is pleasurable, people normally chew for much longer periods of time than they spend brushing or flossing their teeth. Furthermore, chewing gum is especially advantageous for use when toothbrushing is not possible or convenient.

It is well known to the art that mineral adjuvants have been added to chewing gum compositions to act as cleaning and polishing agents, for example, U.S. Pat. No. 4,828,820; 4,170,632 (calcium carbonate) U.S. Pat. No. 4,400,372 (calcined kaolin) and U.S. Pat. No. 3,590,120 (zirconium silicate). The presence of the mineral adjuvants is problematic as such adjuvants are used in high concentrations in the order of 10–40% by weight and have been found to be unduly harsh to tooth enamel.

SUMMARY OF THE INVENTION

In accordance with the present invention there is provided a chewing gum composition capable of whitening and removing stain from teeth which comprises a chewing gum containing from about 0.5 to about 3.0% by weight silica particles, the particles may be precipitated, a silica gel, or a combination of the two, containing about 5 to about 35% by weight water and having:

(i) a mean particle size from about 5 to about 12 microns;

(ii) an Einlehner Hardness of from 1 to about 20;

(iii) an oil absorption value of from about 40 to less than 100 cc/100g;

(iv) a BET surface area from 100 to 700 $m^2/g$ of silica.

Mean particle size is measured using a Malvern Particle Size Analyzer, Model Mastersizer S, Malvern Instruments, Inc., Southborough, Mass. 01772 wherein a helium-neon gas laser beam is projected through a transparent cell which contains the silica particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silica.

Einlehner hardness value is obtained using an Einlehner At-1000 Abrader to measure the softness of the silica in the following manner: A Fourdrinier brass wire screen is weighed and exposed to the action of a 10% aqueous silica suspension for a given number of revolutions. The hardness value is expressed as milligrams weight lost of the Fourdrinier wire screen per 100,000 revolutions.

BET surface area is determined by a BET nitrogen adsorption method described in Brunauer et al., J. Am. Chem. Soc., 60, 309 (1938). The BET measurement is preformed using an Accelerated Surface Area and Porosimetry Analyzer (ASAP 2400), by Micromeritics Instrument Corporation, Norcross, Ga. 30093. The sample is outgassed under vacuum at 350° C. for a minimum of 2 hours before measurement.

Oil absorption values are measured using the ASTM rub-out method D281. All measurement levels are by weight of the total composition, unless otherwise indicated. Additionally, all measurements are made at 25° C., unless otherwise specified.

DETAILED DESCRIPTION OF THE INVENTION

The silica used to prepare the tooth whitening chewing gum compositions of the present invention is comprised of precipitated or colloidal particles of silica having an average particle size ranging from about 3 microns to about 12 microns, and more preferably between about 5 to about 10 microns and a pH range from 4 to 10 preferably 6 to 9 when measured as a 5% by 20 weight slurry.

The silica used to prepare the chewing gum compositions of the present invention is differentiated by means of its oil absorption value, having oil absorption value of less than 100 cc/100g, and preferably in the range of from 45 cc/100g silica to less than 70 cc/100g silica.

A silica particularly useful in the practice of the present invention is marketed under the trade designation Zeodent 105 by J. M Huber Co., Atlanta, Ga. 30327. An example of such silica is Zeodent DP105, a silica precipitate having a water content of 5% by weight averaging from about 7 to about 10 microns in diameter, having an Einlehner Hardness of 5, a BET surface area of 390 $m^2/g$ of silica, an oil absorption of less than 70 $cm^3/100$ g of silica. This silica exhibits low abrasiveness to tooth enamel.

The silica abrasive can be used as the sole abrasive in preparing the chewing gum of the present invention or in combination with other known dentifrice abrasives or polishing agents including calcium carbonate, sodium bicarbonate, sodium metaphosphate, potassium metaphosphate, tricalcium phosphate, dihydrated dicalcium phosphate, bentonite or other siliceous materials, or combinations thereof.

The total quantity of abrasive silica present in the chewing gum composition of the present invention is at a concentration of from about 0.2 to about 5.0% by weight, preferably from about 1.0% to about 3% by weight.

In addition to the silica, the chewing gum composition of the present invention contains additional ingredients found in conventional chewing gum compositions, and at conventional levels. The chewing gum used in the tooth whitening composition of this invention is preferably a sugarless chewing gum since sugarless gums do not promote tooth decay. Chewing gum formulations are well known in the art and typically contain, in addition to, a chewing gum base, one or more plasticizing agents; at least one sweetening agents and at least one flavoring agent.

Gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, or mixtures thereof. Representative synthetic gums or elastomers include butadiene-styrene copolymers, polyisobutylene and isobutylene-isoprene copolymers.

Plasticizing/softening agents commonly used in chewing gum compositions are suitable for use in this invention, including gelatin, waxes and mixtures thereof in amounts of 0.1 to 5% by weight.

The sweetening agent ingredient used in the practice of this invention may be selected from a wide range of materials. Bulk sweeteners such as maltose including partially hydrolyzed starch, corn syrup solids and sugar alcohols such as sorbitol, xylitol, mannitol and mixtures thereof, and high intensity artificial sweeteners such as the soluble saccharin salts, i.e., sodium or calcium saccharin salts, cyclamate salts, such as the sodium salt and the like, and the free acid form of saccharin; dipeptide based sweetening agents such as L-aspartyl-L-phenyl-alanine methyl ester and acesulfame potassium. The bulk sweetener is present in the chewing gum composition of the present invention in amounts of about 40 to about 80 % by weight and preferably about 50 to about 75 % by weight. The high intensity artificial sweetener is present in the chewing gum composition of the present invention in amounts of about 0.1 to about 2% by weight and preferably about 0.3 to 1% by weight.

In addition to the ingredients listed above, the gum compositions may also include conventional additives such as colorants, flavoring agents and the like. For example, titanium dioxide may be utilized as a colorant. A variety of flavors known in the art may be used, including essential oils, such as cinnamon, spearmint, peppermint, menthol, birch, anise and the like; natural fruit flavors derived from the essence of fruits, such as apple, pear, peach, strawberry, cherry, apricot, orange, watermelon, banana and the like; bean-derived flavors, such as coffee, cocoa and the like. Flavoring agents are incorporated in the chewing gum formulation at a concentration of about 0.5 to about 5 % by weight and preferably 1 to 3 % by weight.

Other agents which may be incorporated in the chewing gum compositions of the present invention are agents to counter breath malodor and include water soluble zinc salts (at least 1% soluble) particularly zinc chloride, zinc acetate, zinc citrate and zinc gluconate. The 15 zinc salt is present in amounts which provide about 0.01 to about 1 % by weight zinc ions and preferably about 0.02 to about 0.06% by weight zinc ions. Anticalculus phosphate salts may also be present in the chewing gum compositions of the present invention. Phosphate salts include pyrophosphates, polyphosphates, polyphosphonates and mixtures thereof. The pyrophosphate salts particularly useful in the chewing gum compositions of the present invention include dialkali metal pyrophosphate salts, tetraalkali polyphosphate salts and mixtures thereof. Tetrasodium pyrophosphate, tetrapotassium pyrophosphate and sodium tripolyphosphate are the preferred phosphate salts. The phosphate salts may be present in the chewing gum compositions of the invention in concentrations of about 0.5% to about 7% by weight and preferably about 2 to about 3% by weight.

A sample procedure for formulating the chewing gum composition is as follows: the gum base is first melted in a heated kettle at 55°–65° C. One or more of the sweeteners are then added to the gum base followed by one or more flavors, zinc and phosphate salts the silica and plasticizers or softeners. All ingredients are then mixed for a sufficient period of time to ensure adequate dispersion. The mixture is then allowed to cool and is cut into suitable serving sizes.

The following examples are further illustrate to he present invention, but it is understood that the invention is not limited thereto. All amounts and proportions referred to herein and the appended claims are by weight.

EXAMPLE

A pair of chewing gums designated Chewing Gum A and Chewing gum B were prepared containing the precipitated silica, Zeodent DP105 at concentrations of 2% and 1% by weight respectively. The ingredients of Chewing gum A are listed in Table I below. Chewing gum B contained the same ingredients as Chewing Gum A except 1% by weight of Zeodent DP105 was replaced with 1% by weight sorbitol.

For purposes of comparison, chewing gum C was prepared having the same ingredients as Chewing Gum A except, the 2% by weight Zeodent DP 105 was replaced with 2% by weight sorbitol.

TABLE I

| Ingredients | Wt. % |
| --- | --- |
| Gum base | 25.40 |
| Sorbitol | 26.60 |
| Aspartame | 0.68 |
| Maltitol syrup | 0.60 |
| Acesulfame-K | 0.09 |
| Malitol | 35.20 |
| Xylitol | 5.00 |
| Flavor | 2.42 |
| Zinc gluconate | 0.20 |
| Tetrasodium pyrophosphate | 1.10 |
| Sodium tripolyphosphate | 1.10 |
| Zeodent DP105 | 2.00 |
| Na bicarbonate | 0.50 |
| Titanium dioxide | 0.42 |
| Gelatin | 0.80 |
| Carnauba wax | 0.07 |

To evaluate the whitening efficacy of Chewing Gums A, B and C, squares of dental enamel, 4 mm on a side, were cut from bovine incisors and embedded in clear polyester casting resin to provide 1.5 cm square blocks with the labial surface exposed. In order to render the tooth surfaces more similar to natural teeth and promote the formation of stain on the enamel, the specimens were etched for 60 seconds in 0.2M HCl followed by a final etch with 1% phytic acid for 60 seconds. The etched specimens were rinsed with deionized water and attached to a staining apparatus equipped with a trough designed to provide alternate immersion of the specimens into the trough which contained the staining broth followed by air-drying of the specimens while being rotated in a constant rate of 1.5 revolutions per minute.

The staining broth was prepared by adding 1.02 g of instant coffee, 1.02 g of instant tea, 10 ml of red wine and 0.75 g of gastric mucin to 250 ml of sterilized trypticase soy broth to which was also added 50 ml of a 24-hour *Micrococcus luteus* culture. The apparatus, with the enamel specimens attached thereto was placed in an incubator at 37° C. with the specimens rotating continuously through the staining broth and air. The staining broth was replaced once every 24 hours. With each broth change the trough and specimens were rinsed and the specimens toothbrushed with deionized water to remove any loose deposits. Daily broth changes were continued for 10 to 14 days until the stain on the specimens was sufficiently dark (L* score~35). Then, the specimens were removed from the staining broth, brushed thoroughly with deionized water, and refrigerated in a humidor until used.

The intensity of the extrinsic stain on the teeth was measured by taking color readings with a Minolta spectrophotometer. Measurements over the entire visible color spectrum were obtained using the CIELAB color scale. This scale quantifies color according to 3 parameters, L* (lightness-darkness scale), a* (red-green chroma), and b* (hellow-blue chroma). In order to obtain reproducible readings, the stained enamel specimens were allowed to air-dry at room temperature for 30 minutes before measurements were made.

Measurements were conducted by aligning the center of the 4 mm square segment of stained enamel directly over the 3 mm diameter targeting aperture of a Minolta® spectrophotometer. An average of 3 readings using the L*a*b* scale were taken for each specimen.

Before treatment, the baseline L*a*b* stain scores of the tooth specimens were determined and used to stratify the teeth into balance groups. A mastication device of the type described in Kleber et al, J. Dent. Res. 60:109:114 (1981) designed to simulate human mastication of chewing gum, was used to treat the tooth specimens with the test chewing gum. For testing, a stained tooth specimen was placed both in the upper and lower tooth holders of the instrument. then 15 ml of freshly stimulated human saliva arising from paraffin chewing was placed in the reservoir of the device and warned to 37° C. The saliva and chewing gum were maintained at body temperature for proper chewing consistency during mechanical mastication when the saliva reached the proper temperature, 3 pieces (approximately 5 grams) of chewing gum were inserted between the positioning paddles directly over the lower tooth specimen, the two test teeth were treated with the chewing gum for 20, 60 and 120 minutes. Fresh gum and saliva was used after every 20 minutes in order to simulate the avenge time that gum is normally chewed.

Following each 20-minute treatment period, the specimens were rinsed, allowed to dry 30 minutes, and color readings made. After the last treatment, the specimens were pumiced using a dental handpiece in order to clean all residual stain from the teeth, then color readings were again taken. This final step provided a value for each specimen that represented the maximum amount of stain that potentially could be removed by a test chewing gum.

Stain Calculations:

The overall change in the color of the stained teeth was calculated using the CIELAB equation $\Delta E=[(\Delta L^*)^2+(\Delta a^*)^2+(\Delta b^*)^2]^{1/2}$. The individual components of the L*a*b* scale represent the specific changes in the whiteness (L*), red-green color (a*), and yellow-blue color (b*). The $\Delta E$ value summarized the overall change for each color factor ($\Delta L^*$, $\Delta a^*$, and $\Delta b^*$) and represents the ability of the test chewing gum to remove stain and whiten teeth. The data are calculated and defined as follows:

Stain removed=$\Delta E$ score after treatment

Total stain available=$\Delta E$ score after treatment and pumicing

%Stain removed="stain removed" divided by "total stain available".

The average L*a*b* color scores for the extrinsic stain on the teeth at baseline and after mechanical chewing of the 3 test gums for 20, 60 and 120 minutes are provided in Table II below. The baseline (time 0) data show that all groups were well balanced for each color factor before treatment. Table III below presents the corresponding calculated changes in each color factor at the various chewing treatment times. Chewing gums A and B increased tooth whiteness (larger $\Delta L^*$) significantly better than comparative gum C after 60 and 120 minutes of treatment. Also the chewing gum was significantly more effective in reducing the brown color (larger $\Delta b^*$) than the comparative gum C.

The total amount of stain removed as determined by the overall change in color ($\Delta E$) is shown in Table IV below demonstrating that all 3 chewing gums were significantly effective in removing some stain from the teeth after 20, 60 and 120 minutes of treatment. However, chewing gums A and B were statistically more effective than comparative gum C in removing stain and whitening teeth after both 60 and 120 minutes of treatment. The 120 minute treatment time is representative of a person chewing the gum three separate times for 20 minutes each time. Since the human eye can visually detect a $\Delta E$ color difference of 1 or larger, the amount of stain removed by the chewing gums, especially samples A and B was a very noticeable change.

In order to calculate the percent of stain removed by the chewing gums, all the remaining stain on the test teeth was removed by pumicing them totally clean. An average maximum $\Delta E$ score was then calculated and represents the total amount of removable stain on the test teeth. Based on this score (see Table IV), the Chewing Gum C removed 5, 6 and 10% of the stain on the teeth after mechanical chewing for 20, 60 and 120 minutes, respectively, while Chewing Gum A reduced the stain by 10, 18 and 24% over the same time periods. Chewing Gum B was statistically equivalent to Chewing Gum A and removed 6, 15 and 21% of the stain after 20, 60 and 120 minutes of treatment. The stain reduction scores also demonstrated that Chewing Gums A and B were significantly more effective than the comparative Chewing Gum C. Prior tests with mechanical brushing of similar stained teeth with commercial toothpastes for approximately 5 minutes results in stain reductions of approximately 25 to 50%. Thus Chewing Gums A and B approach the effectiveness of tooth pastes in removing stain from teeth.

TABLE II

Effect of Whitening Chewing Gums on Teeth with Extrinsic Stain

| Treatment Group | Time (min.) | Stain Scores L* | a* | b* |
|---|---|---|---|---|
| A | 0 | 35.96 ± 1.94 | 5.11 ± 0.52 | 6.99 ± 0.59 |
| B | 0 | 36.12 ± 2.30 | 4.31 ± 1.39 | 7.02 ± 2.23 |
| C | 0 | 36.00 ± 0.68 | 4.35 ± 0.64 | 6.96 ± 1.17 |
| A | 20 | 37.33 ± 2.42 | 5.04 ± 0.45 | 8.99 ± 0.98 |
| B | 20 | 37.23 ± 2.97 | 4.78 ± 1.11 | 7.93 ± 1.96 |
| C | 20 | 36.17 ± 0.82 | 3.99 ± 0.84 | 7.60 ± 2.02 |
| A | 60 | 38.81 ± 2.62 | 4.72 ± 0.82 | 10.74 ± 1.23 |
| B | 60 | 39.87 ± 3.24 | 3.90 ± 0.85 | 9.51 ± 2.87 |
| C | 60 | 36.61 ± 1.24 | 4.00 ± 0.69 | 7.84 ± 1.51 |
| A | 120 | 40.09 ± 3.24 | 4.98 ± 0.92 | 11.89 ± 1.29 |
| B | 120 | 41.08 ± 3.77 | 4.30 ± 0.74 | 10.72 ± 2.86 |
| C | 120 | 36.81 ± 1.40 | 3.82 ± 0.84 | 9.01 ± 1.16 |

TABLE III

Extrinsic Stain Removed by Chewing Gums ΔL*, and Δa*, and Δb* Scores

| Treatment Chewing Gum | Chewing Time (min.) | Change in Stain Scores L* | a* | b* |
|---|---|---|---|---|
| A | 20 | 1.37 ± 1.29 | −0.07 ± 0.21 | 2.00 ± 0.90 |
| B | 20 | 1.12 ± 0.88 | 0.47 ± 0.36 | 0.91 ± 0.67 |
| C | 20 | 0.17 ± 0.73 | −0.36 ± 0.24 | 0.64 ± 0.98 |
| A | 60 | 2.85 ± 1.03 | −0.39 ± 0.49 | 3.75 ± 1.35 |
| B | 60 | 3.75 ± 2.83 | −0.41 ± 0.63 | 2.49 ± 2.28 |
| C | 60 | 0.61 ± 1.16 | −0.35 ± 0.21 | 0.88 ± 0.52 |
| A | 120 | 4.12 ± 1.56 | −0.13 ± 0.52 | 4.90 ± 1.47 |
| B | 120 | 4.97 ± 3.04 | −0.01 ± 0.87 | 3.70 ± 2.61 |
| C | 120 | 0.81 ± 1.24 | −0.52 ± 0.40 | 2.05 ± 1.08 |

TABLE IV

Total Change (ΔE) and Reduction (%) in Extrinsic Dental Stain

| Treatment Chewing Gum | Chewing Time (min.) | Total Change (ΔE) in Extrinsic Stain Scores ΔE | Maximum ΔE | Reduction (%) |
|---|---|---|---|---|
| A | 20 | 2.54 ± 1.37 | 28.26 ± 4.43 | 10 |
| B | 20 | 1.75 ± 0.69 | 29.24 ± 4.92 | 6 |
| C | 20 | 1.33 ± 0.45 | 25.57 ± 5.48 | 5 |
| A | 60 | 4.76 ± 1.65 | 28.26 ± 4.43 | 18 |
| B | 60 | 4.59 ± 3.58 | 29.24 ± 4.92 | 15 |
| C | 60 | 1.53 ± 0.66 | 25.57 ± 5.48 | 6 |
| A | 120 | 6.46 ± 2.01 | 28.26 ± 4.43 | 24 |
| B | 120 | 6.40 ± 3.72 | 29.24 ± 4.92 | 21 |
| C | 120 | 2.60 ± 1.00 | 25.57 ± 5.48 | 10 |

What is claimed is:

1. A tooth whitening chewing gum composition which removes stain from the enamel surfaces of teeth comprising:
   (a) about 20 to about 40% by weight of a chewing gum base,
   (b) about 0.5 to about 3.0% by weight of a silica particles, the particles containing about 5 to about 35% by weight water and having:
      (i) a mean particle size from about 5 to about 12 microns;
      (ii) an Einlehner hardness of from 1 to about 20;
      (iii) an oil absorption value of from about 40 to less than 100 cc/100g;
      (iv) a BET surface area from 100 to 700 $m^2/g$ of silica;
   (c) about 0.01 to about 1.0% by weight of a soluble zinc salt,
   (d) the balance of the composition containing plasticizing, sweetening and flavoring agents.

2. The composition of claim 1 wherein the gum contains about 0.5 to about 3.0% by weight of silica:
   (i) a mean particle size from about 5 to about 10 microns;
   (ii) an Einlehner hardness of from 1 to about 20;
   (iii) an oil absorption value of from about 45 to less than 70 cc/100g;
   (iv) a BET surface area from 100 to 700 $m^2/g$ of silica.

3. The composition of claim 1 wherein the silica is present at concentrations in the range of about 1 to about 3% by weight.

4. The composition of claim 1 wherein the composition contains bulk sweeteners are selected from sorbitol, xylitol and maltitol, and artificial sweeteners selected from aspartame and acesulfame potassium.

5. The composition of claim 1 wherein the zinc salt is zinc gluconate.

6. The composition of claim 5 wherein the polyphosphate salt is a mixture of tetrasodium pyrophosphate and sodium tripolyphosphate.

* * * * *